United States Patent
Raman et al.

(10) Patent No.: US 10,932,741 B2
(45) Date of Patent: Mar. 2, 2021

(54) ASSESSING A CONDITION OF A SUBJECT USING NON-CONTRAST DUAL ENERGY COMPUTED TOMOGRAPHY

(71) Applicant: Ohio State Innovation Foundation, Columbus, OH (US)

(72) Inventors: Subha Raman, Columbus, OH (US); Vidhya Kumar, Columbus, OH (US); Orlando Simonetti, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 217 days.

(21) Appl. No.: 16/213,286

(22) Filed: Dec. 7, 2018

(65) Prior Publication Data

US 2019/0175130 A1    Jun. 13, 2019

Related U.S. Application Data

(60) Provisional application No. 62/595,929, filed on Dec. 7, 2017.

(51) Int. Cl.
*G06K 9/00* (2006.01)
*A61B 6/00* (2006.01)
(Continued)

(52) U.S. Cl.
CPC ............ *A61B 6/503* (2013.01); *A61B 6/032* (2013.01); *A61B 6/481* (2013.01); *A61B 6/482* (2013.01);
(Continued)

(58) Field of Classification Search
CPC ......... A61B 6/503; A61B 6/563; A61B 6/507; A61B 6/504; A61B 6/482; A61B 6/481;
(Continued)

(56) References Cited

U.S. PATENT DOCUMENTS

| 9,888,894 B2 * | 2/2018 | Wiedmann | A61B 6/482 |
| 2009/0214095 A1 * | 8/2009 | Wu | G06T 5/002 |
| | | | 382/131 |

(Continued)

OTHER PUBLICATIONS

Bandula, et al., Measurement of myocardial extracellular volume fraction by using equilibrium contrast-enhanced CT: validation against histologic findings, Radiology 269, 2013, 396-403.

(Continued)

*Primary Examiner* — Van D Huynh
(74) *Attorney, Agent, or Firm* — Meunier Carlin & Curftnan LLC

(57) ABSTRACT

In some aspects, the present disclosure relates to a method for non-invasively assessing a myocardial region of a subject by computed tomography (CT). In one embodiment, the method comprises: acquiring non-contrast imaging data for a myocardial region of a subject using dual energy computed tomography (DECT) scanning; reconstructing, from the acquired non-contrast imaging data, monochromatic images for a plurality of energy levels in a range of energy levels; determining, based at least in part on the image reconstruction, attenuation values for each respective energy level of the plurality of energy levels; and performing at least one of detection and quantification of myocardial fibrosis based at least in part on differences in the attenuation values across the plurality of energy levels.

18 Claims, 10 Drawing Sheets
(8 of 10 Drawing Sheet(s) Filed in Color)

(51) Int. Cl.
    G06T 7/00      (2017.01)
    G06T 11/00     (2006.01)
    A61B 6/03      (2006.01)
    A61B 8/08      (2006.01)
(52) U.S. Cl.
    CPC .............. *A61B 6/504* (2013.01); *A61B 6/507* (2013.01); *A61B 6/5205* (2013.01); *A61B 6/5217* (2013.01); *A61B 6/563* (2013.01); *G06T 7/0014* (2013.01); *G06T 11/003* (2013.01); *A61B 6/469* (2013.01); *A61B 8/0883* (2013.01); *G06T 2207/10081* (2013.01); *G06T 2207/30048* (2013.01)
(58) Field of Classification Search
    CPC ..... A61B 6/032; A61B 6/5205; A61B 6/5217; A61B 8/0883; A61B 6/469; G06T 7/0014; G06T 11/003; G06T 2207/10081; G06T 2207/30048; G06T 7/0012; G06T 2211/408; G06T 11/008; G16H 50/30
    USPC ........................................................ 382/131
    See application file for complete search history.

(56) References Cited

U.S. PATENT DOCUMENTS

| | | | | |
|---|---|---|---|---|
| 2011/0280458 | A1* | 11/2011 | Flohr | G06T 5/002 |
| | | | | 382/131 |
| 2014/0010427 | A1* | 1/2014 | Kriston | A61B 6/481 |
| | | | | 382/131 |
| 2014/0050378 | A1* | 2/2014 | Sengupta | G01N 23/046 |
| | | | | 382/131 |
| 2015/0272527 | A1* | 10/2015 | Narayanan | A61B 6/481 |
| | | | | 382/131 |

OTHER PUBLICATIONS

DeAlmeida, et al., Transverse aortic constriction in mice, J Vis Exp JoVE 2010.
Diao, et al., Histologic validation of myocardial fibrosis measured by T1 mapping: a systematic review and meta-analysis, J Cardiovasc Magn. Reson official J Soc Cardiovasc Magn. Reson 18, 2016, 92.
Fukunaga, Introduction to Statistical Pattern Recognition, second ed., 1990, Academic Press; Boston, 124-181.
GE Healthcare Discovery CT750 HD, 2011, 49 pages.
Gulati, et al., Association of fibrosis with mortality and sudden cardiac death in patients with nonischemic dilated cardiomyopathy, J Am Med Assoc 309, 2013, 896-908.
Haaf P, Garg P, Messroghli DR, Broadbent DA, Greenwood JP, Plein S. Cardiac T1 mapping and extracellular volume (ECV) in clinical practice: a comprehensive review. J Cardiovasc Magn Reson. 2016;18:89.
Hong, et al., Myocardial characterization using dual-energy CT in doxorubicin-induced DCM: comparison with CMR t1-mapping and histology in a rabbit model, JACC Cardiovasc imaging 9, 2016, 836-845.
Hubbell and Seltzer. Tables of X-Ray Mass Attenuation Coefficients and Mass Energy-Absorption Coefficients from 1 keV to 20 MeV for Elements Z=1 to 92 and 48 Additional Substances of Dosimetric Interest. NIST Standard Reference Database 126. Last updated Jul. 2004. Available online, internet: https://www.nist.gov/pml/x-ray-mass-attenuation-coefficients (last accessed Dec. 5, 2018).
Johnson, et al., Material differentiation by dual energy CT: initial experience, Eur Radiol 17, 2007, 1510-1517.
Kramer, et al., Standardized cardiovascular magnetic resonance (CMR) protocols 2013 update. Journal of Cardiovascular Magnetic Resonance. 2013;15:91.
Kumar, et al., Computation of calcium score with dual-energy computed tomography: a phantom study, J Comput assisted Tomogr 41, 2017, 156-158.
Kumar, et al., Non-contrast estimation of diffuse myocardial fibrosis with dual energy CT: A phantom study. J Cardiovasc Comput Tomogr. 2018;12:74-80.
Lamb, et al., Stratification of patients with liver fibrosis using dual-energy CT, IEEE Trans Med Imaging 2014.
Mewton, et al., of myocardial fibrosis with cardiovascular magnetic resonance, J Am Coll Cardiol 57, 2011, 891-903.
Nacif, et al., Interstitial myocardial fibrosis assessed as extracellular volume fraction with low-radiation-dose cardiac CT, Radiology 264, 2012, 876-883.
Priori, et al., 2015 ESC guidelines for the management of patients with ventricular arrhythmias and the prevention of sudden cardiac death. The task force for the management of patients with ventricular arrhythmias and the prevention of sudden cardiac death of the European society of cardiology, G Ital Cardiol 17, 2016, 108-170.
Puntmann, et al., T1 mapping in characterizing myocardial disease: a comprehensive review. Circ Res. 2016;119:277-299.
Reynoso, et al., Spectral signal density of carotid plaque using dual-energy computed tomography, J neuroimaging official J Am Soc Neuroimaging, 27, 2017, 511-516.
Rodriguez-Granillo, et al., Detection of myocardial infarction using delayed enhancement dual-energy CT in stable patients, AJR Am J Roentgenol 2017, 1-10.
Saffitz, The pathology of sudden cardiac death in patients with ischemic heart disease—arrhythmology for anatomic pathologists, Cardiovasc Pathol. official J Soc Cardiovasc Pathol. 14, 2005, 195-203.
Schulz-Menger J, Bluemke DA, Bremerich J, et al. Standardized image interpretation and post processing in cardiovascular magnetic resonance: Society for Cardiovascular Magnetic Resonance (SCMR) board of trustees task force on standardized post processing. J Cardiovasc Magn Reson. 2013;15:35.
Stuckey, et al., T(1) mapping detects pharmacological retardation of diffuse cardiac fibrosis in mouse pressure-overload hypertrophy, Circ Cardiovasc imaging 7, 2014, 240-249.
Whittaker, et al., Quantitative assessment of myocardial collagen with picrosirius red staining and circularly polarized light, Basic Res Cardiol 89, 1994, 397-410.
Wong, et al. Association between extracellular matrix expansion quantified by cardiovascular magnetic resonance and short-term mortality. Circulation. 2012;126:1206-1216.
Xue, et al., Motion correction for myocardial T1 mapping using image registration with synthetic image estimation. Magn Reson Med. 2012;67:1644-1655.
Yi, et al., The association between cardiovascular risk and cardiovascular magnetic resonance measures of fibrosis: the Multi-Ethnic Study of Atherosclerosis (MESA), J Cardiovasc Magn. Reson official J Soc Cardiovasc Magn. Reson 17, 2015, 15.
Ying, et al., Characterization of the inflammatory and fibrotic response in a mouse model of cardiac pressure overload, Histochem Cell Biol 131, 2009, 471-481.
Zhang, X. Li and B. Liu, Objective characterization of GE discovery CT750 HD scanner: gemstone spectral imaging mode, Med Phys 38, 2011, 1178-1188.

* cited by examiner

ASSESSING A CONDITION OF A SUBJECT USING NON-CONTRAST DUAL ENERGY COMPUTED TOMOGRAPHY

CROSS-REFERENCE TO RELATED APPLICATIONS

This Application claims priority to, and benefit under 35 U.S.C. § 119(e) of, U.S. Provisional Patent Application No. 62/595,929, filed Dec. 7, 2017, which is hereby incorporated by reference herein in its entirety as if fully set forth below.

STATEMENT REGARDING GOVERNMENT SUPPORT

This invention was made with government support under Grant Nos. HL116533 and HL134616, awarded by the National Institutes of Health. The government has certain rights in this invention.

BACKGROUND

Myocardial fibrosis, a pathologic accumulation of collagen in cardiac muscle, contributes to heart failure, arrhythmias, and death across a broad range of ischemic and non-ischemic heart disease ([1,2]) Detection and quantification of left ventricular (LV) myocardial fibrosis aids in diagnosis and treatment planning for patients with heart failure and cardiomyopathies or those at-risk for arrhythmias ([3]) and can be determined by direct histopathological examination of myocardial tissue or contrast-enhanced magnetic resonance techniques ([4]). Histological analysis requires invasive biopsy to obtain tissue samples, and may be limited by sampling error and high morbidity ([5]). Recent advances in quantitative cardiac magnetic resonance (CMR) mapping techniques offer non-invasive computation of the myocardial extracellular volume fraction (ECV), and have been correlated with the extent of myocardial fibrosis ([6]). However, claustrophobia, non-MR compatible implants and other limitations preclude CMR-based estimates of myocardial fibrosis in a number of patients with known or suspected myocardial disease.

It is with respect to these and other considerations that the various aspects of the present disclosure as described below are presented.

SUMMARY

In some aspects, the present disclosure relates to assessing a subject using dual energy computed tomography (DECT). In accordance with some embodiments of the present disclosure, non-contrast DECT with multi-energy analysis offers strong material discrimination abilities due to inherent differences in attenuation at multiple x-ray energies, without exposure to an exogenous contrast agent. DECT is able to differentiate collagen from other tissues ([7, 8]), and effective and reliable material differentiation is key for quantification of collagen deposition in fibrotic myocardium, making cardiac CT a useful alternative to CMR. Several past studies have utilized both single and dual-energy contrast-enhanced CT techniques to estimate ECV ([9-11]). However, these approaches require exposure to iodinated contrast.

In one aspect, the present disclosure relates to a method for non-invasively assessing a myocardial region of a subject by computed tomography (CT). In one embodiment, the method comprises: acquiring non-contrast imaging data for a myocardial region of a subject using dual energy computed tomography (DECT) scanning; reconstructing, from the acquired non-contrast imaging data, monochromatic images for a plurality of energy levels in a range of energy levels; determining, based at least in part on the image reconstruction, attenuation values for each respective energy level of the plurality of energy levels; and performing at least one of detection and quantification of myocardial fibrosis based at least in part on differences in the attenuation values across the plurality of energy levels.

In one embodiment, the method further comprises performing a linear discriminant analysis on the attenuation values to classify the myocardial fibrosis.

In one embodiment, classifying the myocardial fibrosis comprises determining a classification of the severity of the myocardial fibrosis.

In one embodiment, determining the attenuation values for the plurality of energy levels comprises performing a material decomposition technique.

In one embodiment, the detection and/or quantification of the myocardial fibrosis comprises differentiating collagen from other materials in the myocardial region of the subject.

In one embodiment, the linear discriminant analysis comprises: calculating distances between multi-energy attenuation values in multi-dimensional space; and based on the calculated distances, clustering attenuation values that fall close together in the multi-dimensional space, wherein each cluster shares at least one particular identifying characteristic of an associated material.

In one embodiment, the range of energy levels is from about 40 keV to about 140 keV.

In one embodiment, the dual energies for the CT scanning correspond to x-ray tube voltages of about 80 kVp and about 140 kVp.

In one embodiment, the subject is a human.

In another aspect, the present disclosure relates to a method for non-invasively assessing a region of interest of a subject by computed tomography (CT). In one embodiment, the method comprises: acquiring non-contrast imaging data corresponding to the region of interest of the subject using dual energy computed tomography (DECT) scanning; reconstructing, from the acquired non-contrast imaging data, monochromatic images for a plurality of energy levels in a range of energy levels; determining, based at least in part on the image reconstruction, attenuation values for each respective energy level of the plurality of energy levels; and performing at least one of detection and quantification of a material of interest in tissue of the subject in the region of interest, based at least in part on differences in the attenuation values across the plurality of energy levels.

In one embodiment, the method further comprises performing a linear discriminant analysis on the attenuation values to perform the detection and/or quantification of the material of interest.

In one embodiment, the material of interest in the tissue comprises at least one of iron, fat, inflammatory cells, and amyloid protein.

In one embodiment, the method further comprises identifying and/or classifying a condition of the subject based on the detection and/or quantification of the material of interest.

In one embodiment, the region of interest comprises at least part of the heart, pancreas, liver, spleen, kidney, brain, lungs, skin and/or skeletal muscle of the subject.

In one embodiment, the condition of the subject comprises at least one of myocardial fibrosis, cirrhosis in the liver, fibrosis in the kidney, iron overload in the heart, skeletal muscle, liver, pancreas, or pituitary gland, and amyloidosis in the heart, skin, kidney, brain, or liver.

In one embodiment, determining the attenuation values for the plurality of energy levels comprises performing a material decomposition technique.

In one embodiment, performing the detection and/or quantification of the material of interest in the tissue of the subject comprises differentiating a particular material from other materials in the region of interest of the subject.

In one embodiment, the linear discriminant analysis comprises: calculating distances between multi-energy attenuation values in multi-dimensional space; and based on the calculated distances, clustering attenuation values that fall close together in multi-dimensional space, wherein each cluster shares at least one particular identifying characteristic of an associated material.

In one embodiment, detecting and/or quantifying of the material of interest in the tissue comprises detecting the associated material from a respective at least one shared, particular identifying characteristic.

In one embodiment, the range of energy levels is from about 40 keV to about 140 keV.

In one embodiment, the dual energies for the DECT scanning correspond to x-ray tube voltages of about 80 kVp and about 140 kVp.

In one embodiment, the subject is a human.

Other aspects and features according to the example embodiments of the present disclosure will become apparent to those of ordinary skill in the art, upon reviewing the following detailed description in conjunction with the accompanying figures.

BRIEF DESCRIPTION OF THE DRAWINGS

The patent or application file contains at least one drawing executed in color. Copies of this patent or patent application publication with the color drawing(s) will be provided by the Office upon request and payment of the necessary fee. Reference will now be made to the accompanying drawings, which are not necessarily drawn to scale.

FIG. 1 demonstrates that visual analysis alone of monochromatic images from DECT may not readily distinguish the absence or presence of myocardial fibrosis as can be seen by LGE-CMR.

DETAILED DESCRIPTION

Figure 1:
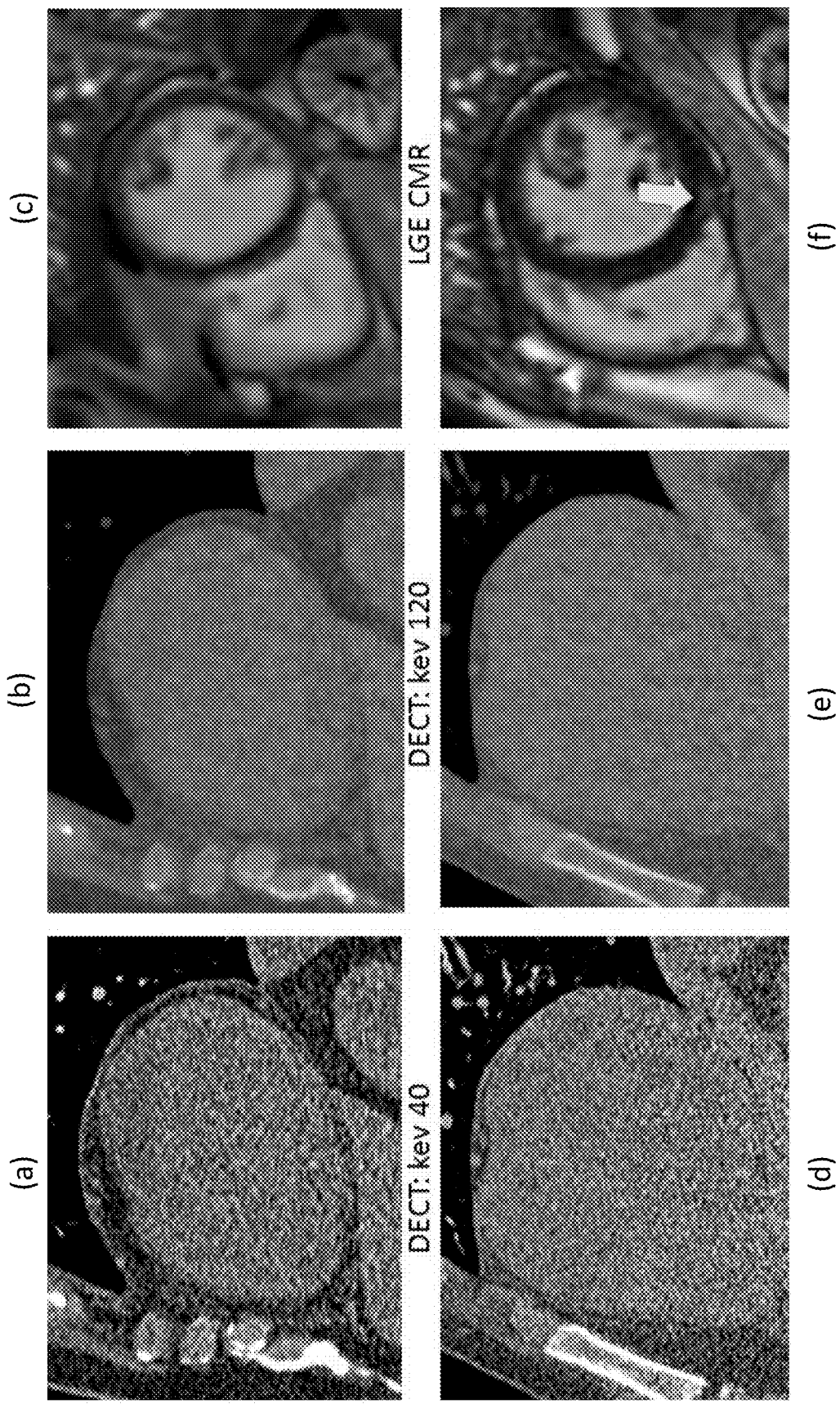
FIG. 1 illustrates, with respect to the example implementations of the present disclosure described for "Example 1", monochromatic images from DECT at 40 and 120 keV (panels (a) and (b)) and LGE CMR (panel (c)) of a region of interest of a subject where myocardial fibrosis is not present. Panels (d) and (e) illustrate monochromatic images from DECT at 40 and 120 keV and LGE CMR (panel (f)) of a region of interest of a subject where myocardial fibrosis is present (see arrow in image of panel (f)).

In some aspects, the present disclosure relates to non-contrast DECT with multi-energy analysis. Although example embodiments of the present disclosure are explained in detail herein, it is to be understood that other embodiments are contemplated. Accordingly, it is not intended that the present disclosure be limited in its scope to the details of construction and arrangement of components set forth in the following description or illustrated in the drawings. The present disclosure is capable of other embodiments and of being practiced or carried out in various ways.

It must also be noted that, as used in the specification and the appended claims, the singular forms "a," "an" and "the" include plural referents unless the context clearly dictates otherwise. By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

Ranges may be expressed herein as from "about" or "approximately" one particular value to "about" or "approximately" another particular value. When such a range is expressed, exemplary embodiments include from the one particular value to the other particular value. As used herein, "about" or "approximately" generally can mean within 20 percent, preferably within 10 percent, and more preferably within 5 percent of a given value or range, and can also include the exact value or range. Numerical quantities given herein can be approximate, meaning the term "about" or "approximately" can be inferred if not expressly stated.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the present disclosure. Similarly, it is also to be understood that the mention of one or more components in a device or system does not preclude the presence of additional components or intervening components between those components expressly identified.

As discussed herein, a "subject" (or "patient") may be any applicable human, animal, or other organism, living or dead, or other biological or molecular structure or chemical environment, and may relate to particular components of the subject, for instance specific organs, tissues, fluids, elements, or other biological and/or chemical related components (which may generally be referred to herein as, or with respect to, a "material". The particular components may be in a particular location of the subject, sometimes referred to herein in relation to a "region of interest" (ROI) or "area of interest".

Some references, which may include various patents, patent applications, and publications, are cited in a reference list and discussed in the disclosure provided herein. The citation and/or discussion of such references is provided merely to clarify the description of the present disclosure and is not an admission that any such reference is "prior art" to any aspects of the present disclosure described herein. In terms of notation, "[n]" corresponds to the $n^{th}$ reference in the list. For example, [3] refers to the $3^{rd}$ reference in the list, namely Priori S G, Blomstrom-Lundqvist C, Mazzanti A, et al. 2015 ESC guidelines for the management of patients with ventricular arrhythmias and the prevention of sudden cardiac death. G Ital Cardiol. 2016; 17:108-170. All references cited and discussed in this specification are incorporated herein by reference in their entireties and to the same extent as if each reference was individually incorporated by reference.

A detailed description of aspects of the present disclosure, in accordance with various example embodiments, will now be provided with reference to the accompanying drawings. The drawings form a part hereof and show, by way of illustration, specific embodiments and examples. In referring to the drawings, like numerals represent like elements throughout the several figures.

Generally a CT system for medical imaging applications operates by emitting X-ray beam(s) (e.g., ranging from 70 to 140 kVp) from X-ray source(s), that are received by corresponding detector(s). The inherent contrast of the image dataset generated by this process depends on differences in photon attenuation of the various materials that constitute the human body (e.g., soft tissue, air, calcium, fat). The degree that a material will attenuate the X-ray beam is dependent on factors including tissue composition and photon energy level and how closely it exceeds the k-edge, i.e., inner electron shell binding energy, of the material. Tissue attenuation can therefore be manipulated by changing photon energy levels. In dual energy computed tomography (DECT), two energy levels (e.g., 80 and 140 kVP) are used to acquire images that can be processed to generate additional datasets.

Certain aspects and embodiments of the present disclosure can be performed using a dual energy computed tomography (DECT) system, which may include a commercially available DECT system. Some particular embodiments and example implementations described herein utilize a dual energy, multi-detector, single source scanner with kVp switching capabilities, such as a CT 750 HD system available from GE Healthcare, Waukesha, Wis. However, it should be appreciated that various aspects according to the present disclosure may be performed using a dual-source DECT system. One example of a currently available dual-source DECT system is the Somatom Definition Flash available from Siemens Medical Solutions, Forcheim, Germany. Whereas a single source DECT system can use a single X-ray tube that rapidly alternates between low and high energies (fast-switching) and a single detector that quickly registers information from both energies, a dual source DECT system can use two X-ray tubes and two detectors to obtain simultaneous dual energy acquisition and data processing.

One or more data acquisition or data collection steps as described herein in accordance with one or more embodiments may include acquiring, collecting, receiving, or otherwise obtaining data such as imaging data corresponding to a region of interest. By way of example, data acquisition or collection may include acquiring data via a data acquisition device (e.g., medical imaging system such as a CT system), receiving data from an on-site or off-site data acquisition device or from another data collection, storage, or processing device. Similarly, data acquisition or data collection devices of a system in accordance with one or more embodiments of the present disclosure may include any device configured to acquire, collect, or otherwise obtain data, or to receive data from a data acquisition device within the system, an independent data acquisition device located on-site or off-site, or another data collection, storage, or processing device.

In some aspects, the present disclosure relates to non-contrast DECT with multi-energy analysis, which offers strong material discrimination abilities due to inherent differences in attenuation at multiple x-ray energies, without exposure to an exogenous contrast agent. In some aspects, the present disclosure relates to non-invasively assessing a region of interest of a human subject by DECT with multi-energy analysis. In some embodiments, DECT scanning can be used to acquire non-contrast imaging data corresponding to the region of interest of the subject. From the acquired non-contrast imaging data, monochromatic images can be reconstructed for a plurality of energy levels in a certain range of energy levels. Based at least in part on the image reconstruction, attenuation values can be determined for each respective energy level. Detection and/or quantification of a material of interest (e.g, material in a tissue of the subject) can be performed for the region of interest of the subject, based at least in part on differences in the attenuation values across the plurality of energy levels.

The detection and/or quantification of the material of interest can be used for identifying and/or classifying a condition (e.g., abnormal condition) of the subject. The material of interest in the tissue can be, but is not limited to, one or more of iron, fat, inflammatory cells, and amyloid protein, and the region of interest can be or comprise at least part of an organ of the subject, for example the heart, pancreas, liver, spleen, kidney, brain, lungs, skeletal muscle, and/or skin of the subject. The identified and/or classified condition of the subject can be, but is not limited to, one or more of: fibrosis (e.g., myocardial fibrosis, cirrhosis in the liver, fibrosis in the kidney); iron overload, which can affect the heart, liver, spleen, pancreas, and certain parts of the brain (e.g., pituitary gland); and/or amyloidosis, as different amyloid proteins may affect different organs, such as the heart, skin, liver, kidneys, and brain. Attenuation values vary by material(s) and tissue(s) of interest. In order to predict attenuation values for individual materials, in some embodiments, data from the NIST's X-ray attenuation databases ([28]) may be utilized.

Figure 7:
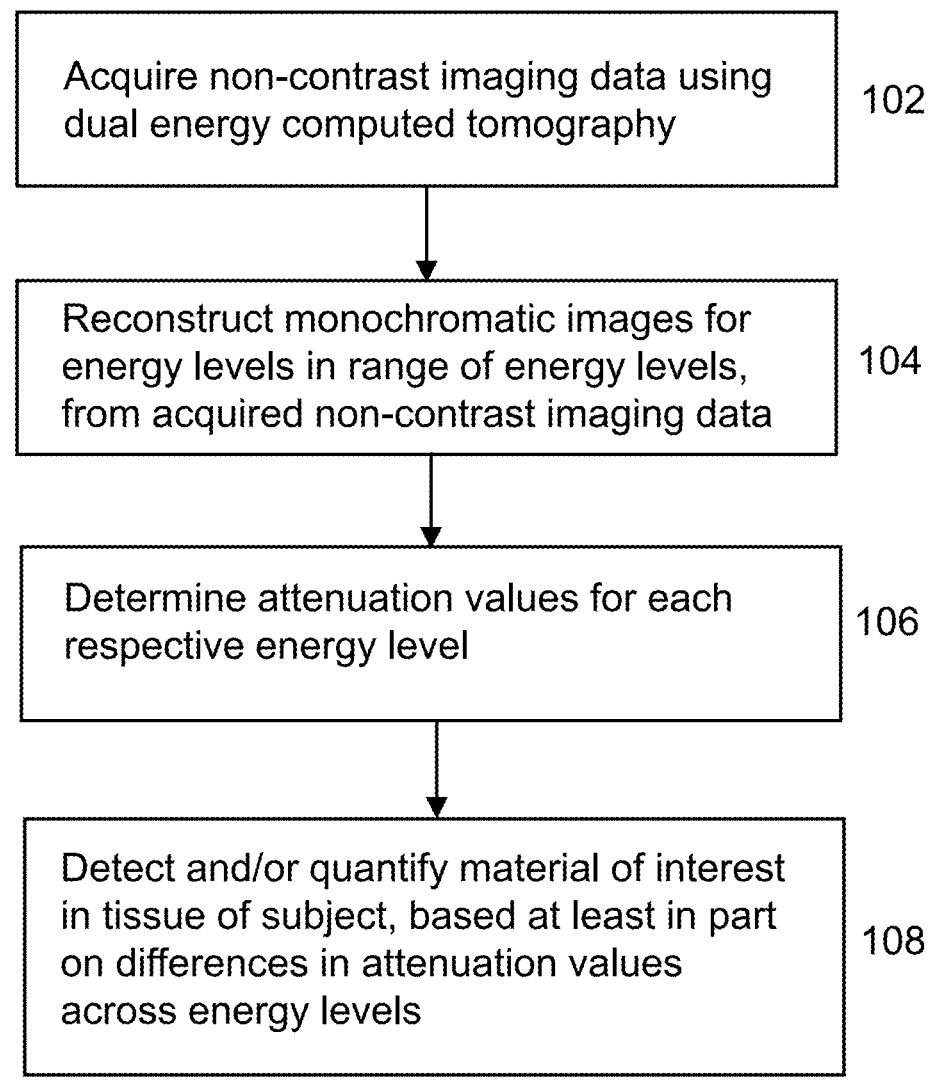
FIG. 7 is a flow diagram illustrating operations of a method according to one embodiment of the present disclosure.

Now referring to FIG. 7, FIG. 7 is a flow diagram illustrating operations of a method 100 according to one embodiment of the present disclosure. At 102, dual energy computed tomography (DECT) scanning is used to acquire non-contrast imaging data corresponding to a region of interest of a subject. At 104, from the acquired non-contrast imaging data, monochromatic images are reconstructed for a plurality of energy levels in a range of energy levels. At 106, based at least in part on the image reconstruction, attenuation values are determined for each respective energy level of the plurality of energy levels. At 106, detection and/or quantification of a material of interest in tissue of the subject is performed for the region of interest of the subject, based at least in part on differences in the attenuation values across the plurality of energy levels.

Figure 8:
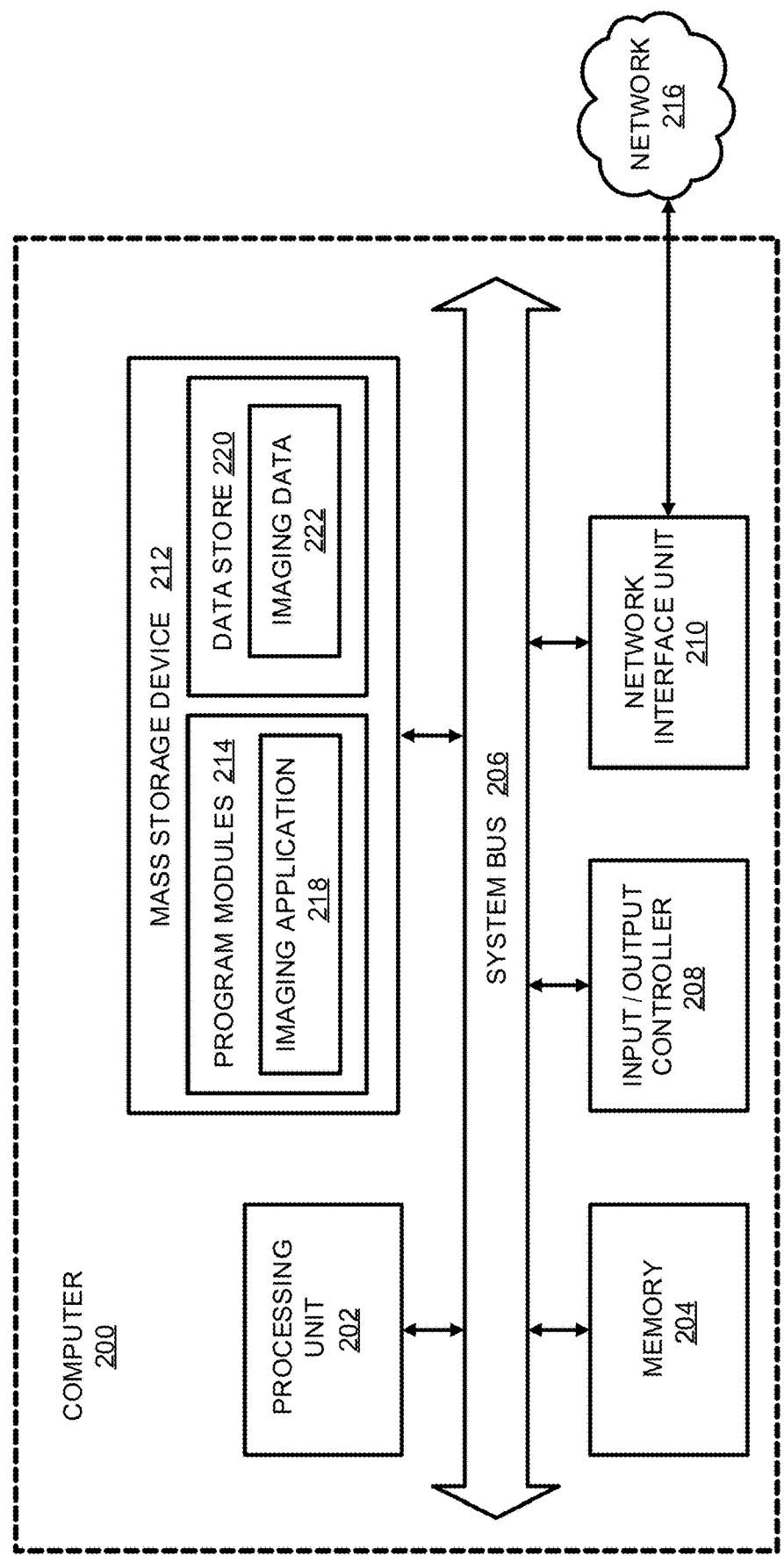
FIG. 8 is a diagram of a computing system capable of implementing aspects of the present disclosure in accordance with one or more embodiments.

In some embodiments, one or more aspects of assessing a subject (e.g., to assess a condition of the subject and/or to assess the presence and/or quantity of a material in tissue of the subject) using non-contrast dual energy computed tomography with multi-energy analysis, according to various embodiments described herein, may be implemented using a computing system, for instance using one or more components of the computing system 200 shown in FIG. 8. DECT implementations in accordance with various embodiments described herein may utilize, or a corresponding DECT system used for the various operations may include and utilize, one or more components of the computer 200, for example to perform one or more functions associated with embodiments illustrated in one or more of FIGS. 1-7. It should be appreciated that the computer 200 may be implemented within a single computing device or a computing system formed with multiple connected computing devices.

As shown, the computer 200 includes a processing unit 202 ("CPU"), a system memory 204, and a system bus 206 that couples the memory 204 to the CPU 202. The computer 200 further includes a mass storage device 212 for storing program modules 214. The program modules 214 may be operable to perform functions associated with embodiments illustrated in one or more of FIGS. 1-7 discussed herein. The program modules 214 may include an imaging application 218 for causing a DECT system to perform data acquisition, and/or for performing processing functions as described herein, for example to acquire and/or process image data corresponding to CT imaging of a region of interest (ROI). The computer 200 can include a data store 220 for storing data that may include imaging-related data 222 such as acquired data from the implementation of DECT in accordance with various embodiments of the present disclosure.

The mass storage device 212 is connected to the CPU 202 through a mass storage controller (not shown) connected to the bus 206. The mass storage device 212 and its associated computer-storage media provide non-volatile storage for the computer 200. Although the description of computer-storage media contained herein refers to a mass storage device, such as a hard disk or CD-ROM drive, it should be appreciated by those skilled in the art that computer-storage media can be any available computer storage media that can be accessed by the computer 200. "Computer storage media", "computer-readable storage medium" or "computer-readable storage media" as described herein do not include transitory signals.

According to various embodiments, the computer 200 may operate in a networked environment using connections to other local or remote computers through a network 216 via a network interface unit 210 connected to the bus 206. The network interface unit 210 may facilitate connection of the computing device inputs and outputs to one or more suitable networks and/or connections such as a local area network (LAN), a wide area network (WAN), the Internet, a cellular network, a radio frequency (RF) network, a Bluetooth-enabled network, a Wi-Fi enabled network, a satellite-based network, or other wired and/or wireless networks for communication with external devices and/or systems. The computer 200 may also include an input/output controller 208 for receiving and processing input from any of a number of input devices. Input devices may include one or more of keyboards, mice, stylus, touchscreens, microphones, audio capturing devices, and image/video capturing devices. An end user may utilize the input devices to interact with a user interface, for example a graphical user interface, for managing various functions performed by the computer 200. The bus 206 may enable the processing unit 202 to read code and/or data to/from the mass storage device 212 or other computer-storage media.

Example Implementations and Corresponding Results

Various aspects of the present disclosure may be still more fully understood from the following description of example implementations and corresponding results and FIGS. 1-6. Some experimental data are presented herein for purposes of illustration and should not be construed as limiting the scope of the present disclosure in any way or excluding any alternative or additional embodiments.

Example 1 relates to non-contrast DECT used in evaluation of myocardial fibrosis in human subjects with varying severity of diffuse and localized fibrosis. Example 2 relates to non-contrast DECT used in non-invasively estimating the extent of diffuse myocardial fibrosis in phantom and animal models.

Example 1

The following describes an example implementation of certain aspects of the present disclosure in which a non-contrast dual-energy CT (DECT) with multi-energy analysis method is discussed. Preclinical data obtained in accordance with aspects described below for the example implementation of "Example 2" supports the ability for predicting the severity of myocardial fibrosis in an animal model of hypertensive heart disease with diffuse fibrosis ([21]). In this present Example 1, a non-contrast DECT approach with multi-energy data analysis is implemented for human subjects. The approach can be utilized to predict myocardial fibrosis in human subjects in vivo, and outperforms single-energy CT techniques for characterization of myocardial fibrosis.

Methods

Subject Recruitment & Enrollment

Twenty-eight subjects were enrolled in this study (see Table 1). Patients ≥18 years of age clinically referred for CMR with myocardial T1 mapping and late gadolinium enhancement (LGE) imaging at a single center were prospectively screened for enrollment.

Image Acquisition

Subjects underwent prospectively-triggered cardiac CT on a 64-slice multi-detector, single source scanner (CT 750 HD, GE Healthcare, Waukesha, Wis.) with kVp switching capabilities yielding interleaved acquisition between 80 and 140 kVp. Images were acquired with detector coverage of 40 mm, slice thickness of 2.0 mm and matrix size of 512 in gemstone spectral imaging (GSI) mode ([15]). Clinically-acquired CMR was performed on a 1.5 T scanner (MAGNETOM Avanto, Siemens Medical Solutions, Malvern, Pa.). Late gadolinium enhancement (LGE) was acquired 12-15 min post-intravenous administration of gadolinium-based contrast agent (gadobutrol 0.15 mmol/kg) in short-axis and long axis cardiac planes with appropriate inversion time selection ([22]). Pre-contrast and post-LGE contrast T1 mapping used a modified look-locker pulse sequence (MOLLI) ([23]) in the identical mid-short axis plane.

TABLE 1

Study Population

| Variable | Value |
|---|---|
| Age, years | 58 ± 13 |
| Male, N (%) | 14 (50) |
| Body mass index, kg/m² | 27.9 ± 5.4 |
| Diabetes, N (%) | 4 (14) |
| Current or former smoker, N (%) | 11 (39) |
| Hypertension, N (%) | 15 (54) |
| Cardiac magnetic resonance indication, N (%) | |
| chest pain | 6 (21) |
| cardiomyopathy | 16 (57) |
| left ventricular hypertrophy | 3 (11) |
| viability | 3 (11) |

Image Processing and Analysis

Images were analyzed by experienced staff blinded to clinical information. Two experienced readers provided consensus review of LGE images, assigning the mid-inferoseptal segment as LGE positive or negative. Myocardial and blood T1 values were recorded from pre- and post-contrast T1 maps, using a region of interest (ROI) within the mid-inferoseptal segment ([24]) for myocardial values and ROI within the LV cavity for blood values. Extracellular volume fraction (ECVcmr) was calculated using the following formula and hematocrit value recorded at the CMR exam, using 29% as a cutoff for normal ([25]).

$$ECVcmr = 100 * (1 - \text{hematocrit}) * \frac{\left(\frac{1}{T1_{tissue,post-contrast}} - \frac{1}{T1_{tissue,native}}\right)}{\left(\frac{1}{T1_{blood,post-contrast}} - \frac{1}{T1_{blood,native}}\right)}$$

DECT images were post-processed and analyzed using GE's AW software, which provides monochromatic reconstructions over the range of 40-140 keV in 10 keV increments using the material decomposition method. Multiplanar reformatting was performed to generate a mid-short axis DECT image comparable to the mid-short axis plane by CMR. For each subject, an ROI drawn in the mid-inferoseptal myocardial segment—consistent with CMR myocardial postprocessing guidelines [(26)]—yielded attenuation values (Hounsfield units, HU) at each energy level that could be exported for further computational analysis. A second level of post-processing was performed in Matlab to remove pixels containing with HU<−1000 (e.g., fat) or >300 (e.g., calcium). Finally, mean and standard deviation of CT attenuation values at each energy value were calculated for the mid-inferoseptal myocardium.

Analysis

Statistical analysis was performed with STATA v12.0 (College Station, Tex.). Multivariate analysis of variance (MANOVA) was performed to assess whether the mean CT attenuation values differed between LGE-negative vs. LGE-positive individuals (see Table 2) or between normal ECV (<29%) and abnormal ECV 29%) ([27]) groups (see Table 3). Linear discriminant analysis (LDA) ([16]) was the main statistical tool used for classification of enhancement and ECV in the inferoseptal segment. Linear discriminant analysis (LDA) is a statistical tool that can be used for classification of collagen content. The distances between multi-dimensional data points (multi-energy attenuation values in our application) are calculated. Sets of points that fall close together in the multi-dimensional space might share a particular identifying characteristic and are classified as clusters. LDA was performed using the post-processed mean CT attenuation value obtained from ROI measurements for each enrolled patient. LDA tested the ability of single energy (70 keV) values, multi-energy predictors, and CT attenuation values, to correctly discriminate between fibrosis severity classes determined by qualitative expert review of LGE images and between normal/abnormal quantitative ECV. Preliminary testing of classifiers was performed using a prospective LDA method, which returned a predicted grouping based on CT characteristics for each enrolled patient. Correct and incorrect classification rates were calculated as a proportion of total data.

TABLE 2

Non-contrast DECT Attenuation Values Across Reconstructed Energy Levels by LGE Group

| | Energy Level | | | | |
|---|---|---|---|---|---|
| | 40 keV | 50 keV | 60 keV | 70 keV | 80 keV |
| LGE-negative | 57.7 ± 34.2 | 52.9 ± 19.2 | 47.3 ± 11.5 | 44.4 ± 7.0 | 45.6 ± 6.0 |
| LGE-positive | 50.2 ± 21.1 | 44.6 ± 13.8 | 40.4 ± 9.6 | 38.0 ± 8.6 | 37.3 ± 7.4 |

| | Energy Level | | | | |
|---|---|---|---|---|---|
| | 90 keV | 100 keV | 110 keV | 120 keV | 130 keV | 140 keV |
| LGE-negative | 46.1 ± 7.6 | 45.6 ± 8.6 | 45.2 ± 9.4 | 44.9 ± 10.0 | 44.7 ± 10.5 | 44.5 ± 10.9 |
| LGE-positive | 36.7 ± 7.3 | 36.1 ± 7.3 | 35.6 ± 7.4 | 35.3 ± 7.5 | 35.1 ± 7.6 | 34.9 ± 7.7 |

TABLE 3

Non-contrast DECT Attenuation Values Across Reconstructed Energy Levels by ECV Group

| | Energy Level | | | | |
|---|---|---|---|---|---|
| | 40 keV | 50 keV | 60 keV | 70 keV | 80 keV |
| ECV < 29% | 56.7 ± 22.9 | 49.8 ± 15.4 | 44.5 ± 9.9 | 41.4 ± 7.3 | 40.7 ± 7.3 |
| ECV ≥ 29% | 47.7 ± 27.3 | 44.1 ± 15.5 | 40.2 ± 10.6 | 38.2 ± 9.3 | 38.9 ± 8.3 |

| | Energy Level | | | | | |
|---|---|---|---|---|---|---|
| | 90 keV | 100 keV | 110 keV | 120 keV | 130 keV | 140 keV |
| ECV < 29% | 40.0 ± 7.7 | 39.3 ± 7.5 | 38.7 ± 7.5 | 38.3 ± 7.5 | 38.0 ± 7.5 | 37.8 ± 7.5 |
| ECV ≥ 29% | 38.9 ± 9.2 | 38.5 ± 10.0 | 38.3 ± 10.7 | 38.0 ± 11.2 | 37.9 ± 11.6 | 37.8 ± 11.9 |

Results

Twenty-eight patients, age 58±13 years and 50% male, were prospectively enrolled to undergo DECT prior to clinically-acquired CMR (see Table 1). Body weight averaged 83.3±21.9 kg. Cardiomyopathy was the most common indication for CMR in this cohort. Myocardial fibrosis was visually apparent by LGE-CMR in 19 (68%). Nine patients had myocardial ECV exceeding the 29% threshold for normal ECV. Average effective radiation dose per non-contrast cardiac DECT scan was 4.7±0.68 mSv, and all DECT image sets were adequate in image quality for analysis.

MANOVA using attenuation values alone did not distinguish between LGE-positive and LGE-negative patients, or between normal ECV and abnormal ECV patients. Single and multi-energy LDA analysis using presence/absence of myocardial fibrosis by LGE as a grouping variable returned correct classification rates of 71% and 89%, respectively. Single and multi-energy LDA analysis using normal/abnormal ECV as a grouping variable returned correct classification rates of 70% and 89%, respectively.

Discussion

Using a novel multi-energy analysis approach to analyzing non-contrast cardiac DECT images in accordance with example implementations of the present disclosure, the inventors have shown in a pilot cohort of patients that the multi-energy analysis approach is superior to single energy-based acquisition and analysis in classifying presence or absence of discrete myocardial fibrosis and diffuse interstitial expansion by CMR. This was achieved with a radiation dose for the dual-energy acquisition in the range of non-contrast cardiac CT scans for coronary calcium scoring or contrast-enhanced myocardial perfusion CT scans. With the inventors' prior work showing that DECT yields comparable coronary artery calcium scores as usual single energy scan protocols ([17]), the present example implementation described here in Example 1 further advances the utility of non-contrast cardiac DECT for myocardial fibrosis assessment. The inventors note that this acquisition technique produced images of sufficient quality to perform multi-energy analysis in normal to obese individuals, an important consideration in the cardiovascular patient population.

Example 2

The following describes an example implementation of certain aspects of the present disclosure, in which non-contrast DECT with multi-energy analysis is used in non-invasively estimating the extent of diffuse myocardial fibrosis in phantom and animal models. In some embodiments, a DECT-based approach is used to estimate myocardial collagen content which utilizes multi-energy information and statistical classifiers to differentiate between increasing severity of fibrosis from a single non-contrast scan.

Methods

Phantom Studies

Type I collagen tablets (GNC, New York) were crushed, the coating removed and the remaining contents dissolved in saline to produce a 500 mg/ml stock solution. Bovine myocardium was divided into 5 mm thick slices. Epicardial fat was removed and myocardium was homogenized using a Kinematica (Luzern, Switzerland) tissue homogenizer. Varying concentrations of stock collagen solution were added to 5 ml of homogenized tissue to obtain 0, 7, 10, 15, 20, 30, 40 and 62% collagen phantoms by mass. Collagen concentrations were chosen to encompass the range of fibrosis observed in a small animal model, and to include values outside of the established range to evaluate the sensitivity of the DECT quantification method ([12]).

Animal Model

Fibrosis in murine myocardium was induced in C57Bl/6 mice using transverse aortic constriction (TAC) ([13]) surgery, which reliably produces myocardial remodeling with diffuse fibrosis enriched for Type I collagen in hypertrophied left ventricular myocardium. The extent of fibrosis in this model increases with time after surgery, thus the mice were stratified into three groups based on the time elapsed post-surgery. The three experimental groups were: i) control (sham procedure, n=7), ii) developing fibrosis (5 weeks of TAC, n=4), and iii) significant fibrosis (8 weeks of TAC, n=4) ([14]). Echocardiography was performed on lightly anesthetized (1.5% isoflurane), 5-week TAC and sham mice using a VEVO 2100 Visual Sonics system (Visual Sonics, Toronto). Left ventricular ejection fraction (EF) and fractional shortening were recorded to confirm that TAC surgery was effective and to monitor the progression of remodeling. Animals were sacrificed immediately prior to ex vivo DECT imaging on freshly harvested hearts. Heart weight, lung weight and tibial length were measured.

Histology

Figure 2:
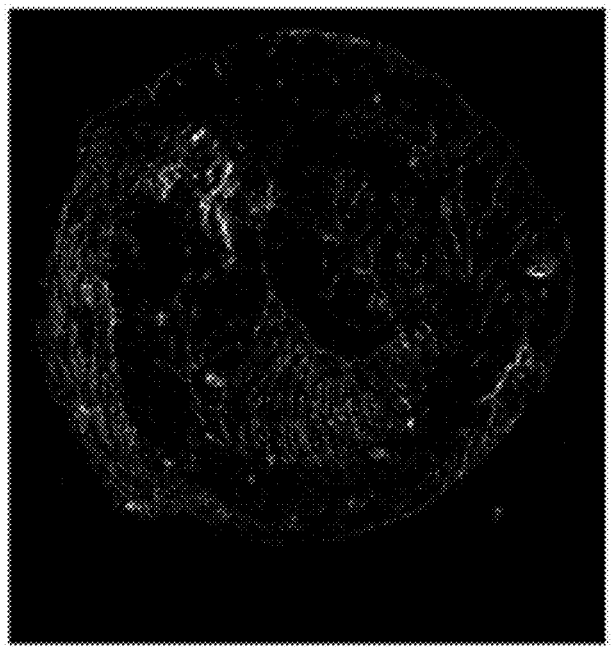
FIG. 2 shows, with respect to the example implementations of the present disclosure described for "Example 2", a histology tissue section with trichrome stain (left) and a post-processed histology image (right). Matlab color thresholding tools allow calculation of total myocardial pixels as the sum of non-white (e.g., red-myocardium and blue-collagen) pixels on the original image (left). Blue-staining collagen is rendered as white pixels on the thresholded image (right). Collagen volume fraction (CVF) is the ratio of collagen-stained pixels to the total pixels.
Figure 2:
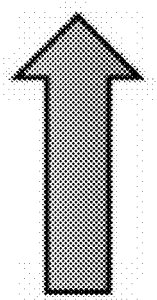
Figure 2:
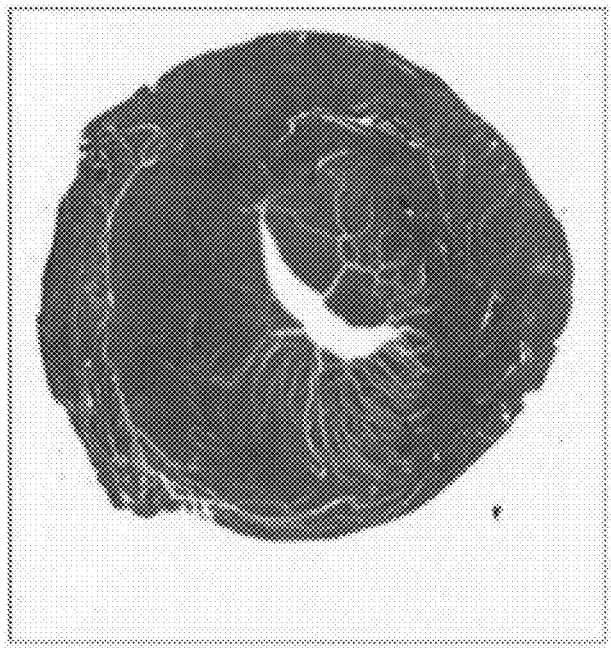
Figure 3:
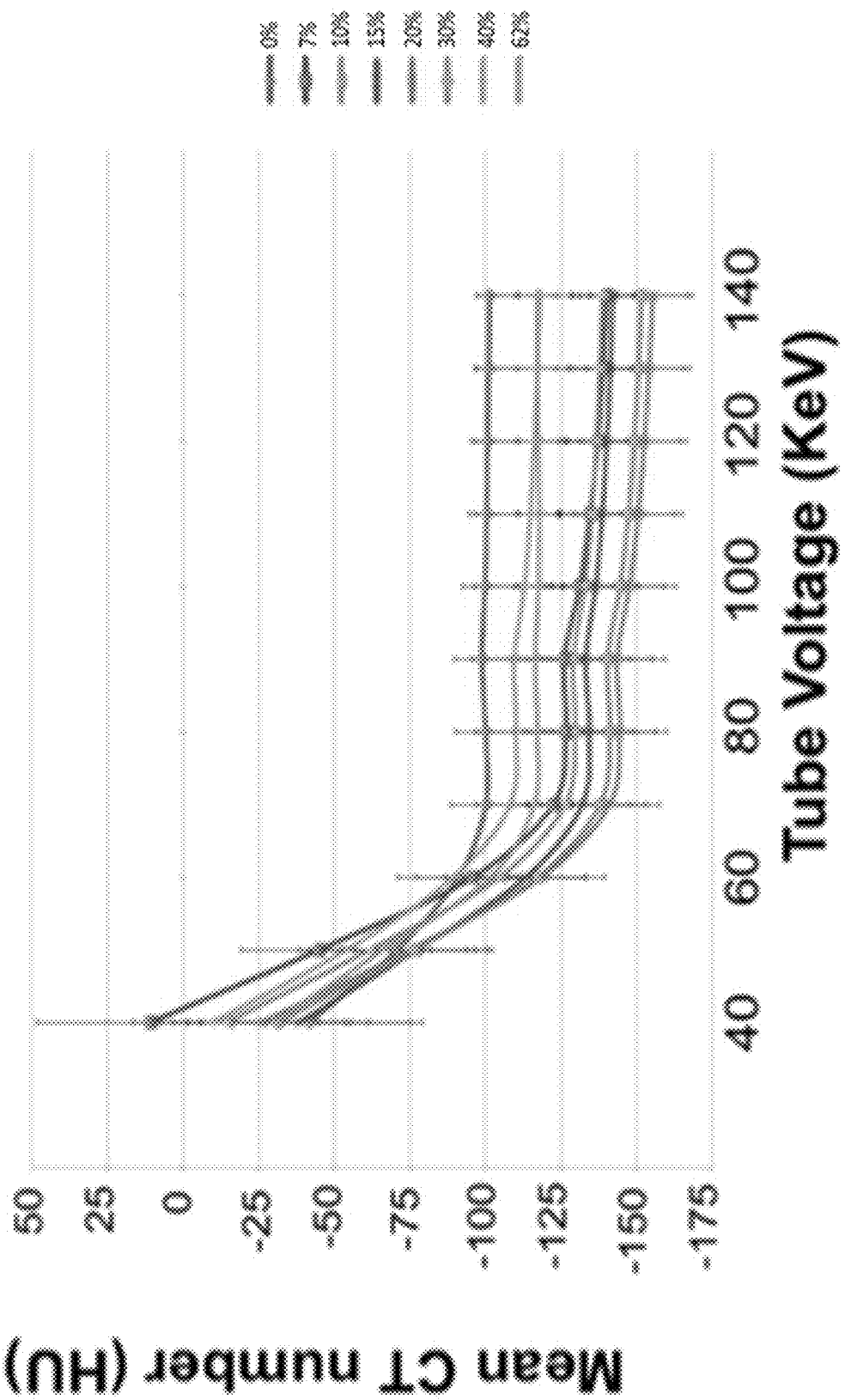
FIG. 3 shows, with respect to the example implementations of the present disclosure described for "Example 2", mean ROI attenuation of each phantom (consisting of homogenized bovine myocardium and collagen solution), plotted across reconstructed energies, where error bars represent standard deviations.

Following DECT imaging, harvested hearts were sectioned for histological analysis. Sections reserved for histology were fixed in 10% buffered formalin, embedded in paraffin, and sliced into five-micron sections. Slices were stained with hematoxylin/eosin (H&E) and Masson's trichrome. Images were acquired with a PathScan Enabler IV pathology slide scanner (Meyer Instruments). Collagen volume fraction (CVF) was obtained from whole slice images; positively stained pixels were calculated as a fraction of total pixels using available image processing tools (Matlab, The Mathworks, Natick, Mass.) (FIG. 2).

Dual Energy CT

All imaging was performed on a 64-slice multi-detector, single source scanner with kVp switching capabilities (CT 750 HD, GE Healthcare, Waukesha, Wis.). Dual energy imaging was performed using an interleaved acquisition with tube voltages 80 and 140 kVp, tube current 640 mA, switching time of 0.2 s and a gantry rotation time of 0.35 s. Images were acquired with detector coverage of 40 mm, slice thickness of 0.625 mm and matrix size of 512 ([15]). Gated DECT acquisition involves prospective electrocardiographic (ECG) triggering, i.e., acquisition at a fixed point in the cardiac cycle based on detection of an ECG signal that is not present in phantoms or postmortem hearts. Therefore, a simulated ECG waveform at 70 bpm was used to trigger both phantom and ex vivo animal DECT acquisitions. Phantom and ex vivo samples were scanned in 2 ml screw-top tubes (ThermoFisher Scientific, Waltham, Mass.) without any additional fluid; the samples were scanned in air.

Post Processing

Dual energy acquisitions were reconstructed into monochromatic images in the range of 40-140 keV with increments of 10 keV using AW software (GE Healthcare; Waukesha, Wis.). Monochromatic reconstructions were generated using the material decomposition method. The material decomposition method utilizes basis materials, iodine and water, for which the relationship between material density and attenuation is known ([15]). By transforming the attenuation of each acquired pixel at high and low kVp acquisitions into the corresponding density of basis materials, behavior at any energy level can be approximated to render monochromatic reconstructions. Reconstructions were generated with a slice thickness of 0.625 mm. Regions of interest (ROIs) of approximately 200 mm$^2$ were drawn to encompass the entire phantom volume or explanted myocardium. Edges of the plastic tube were avoided, though the ROI may have included air. CT attenuation values (Hounsfield units, HU) for each pixel at all monochromatic energy levels within the ROI were exported. Attenuation values were then postprocessed to remove pixels containing only air (HU<−1000) and artifacts from tube edges (HU>3000). Mean and standard deviation of attenuation values at each energy level were calculated for all phantoms (see Table 4 and FIG. 5) and ex vivo samples (see Table 5 and FIG. 6).

TABLE 4

Mean attenuation values ± standard deviation (HU) at every reconstructed energy level for each collagen phantom

| Collagen Concentration (%) | 90 keV | 100 keV | 110 keV | 120 keV | 130 keV | 140 keV |
| --- | --- | --- | --- | --- | --- | --- |
| 0 | −392.9 ± 53.3 | −397.8 ± 53.0 | −401.6 ± 51.6 | −403.7 ± 51.3 | −404.8 ± 50.9 | −405.5 ± 50.8 |
| 7 | −612.8 ± 62.1 | −623.0 ± 60.6 | −628.6 ± 59.7 | −631.8 ± 59.9 | −634.2 ± 60.2 | −635.6 ± 60.6 |
| 10 | −549.2 ± 73.9 | −560.3 ± 75.1 | −566.5 ± 75.5 | −570.6 ± 75.7 | −573.7 ± 76.0 | −575.6 ± 76.2 |
| 15 | −593.9 ± 81.5 | −604.3 ± 79.2 | −610.5 ± 77.5 | −614.0 ± 76.8 | −616.5 ± 76.2 | −617.7 ± 76.1 |
| 20 | −656.1 ± 15.1 | −666.7 ± 16.2 | −671.9 ± 17.6 | −675.1 ± 18.3 | −677.0 ± 19.2 | −678.3 ± 19.6 |
| 30 | −533.8 ± 30.9 | −542.2 ± 31.2 | −547.2 ± 31.1 | −549.8 ± 31.2 | −552.1 ± 31.1 | −553.3 ± 31.0 |
| 40 | −538.8 ± 15.1 | −549.5 ± 16.2 | −555.9 ± 17.6 | −559.7 ± 18.3 | −562.0 ± 19.2 | −563.7 ± 19.6 |
| 62 | −549.4 ± 24.1 | −560.6 ± 24.5 | −567.2 ± 25.6 | −570.8 ± 26.3 | −573.4 ± 26.8 | −575.2 ± 27.1 |

TABLE 5

Mean attenuation values ± standard deviation (HU) at every reconstructed energy level for the TAC fibrosis model

| TAC Week | 40 keV | 50 keV | 60 keV | 70 keV | 80 keV |
| --- | --- | --- | --- | --- | --- |
| 0 week | −692.5 ± 271.6 | −716.0 ± 259.7 | −761.4 ± 251.3 | −775.5 ± 247.7 | −772.5 ± 248.6 |
| 5 week | −702.0 ± 251.4 | −710.6 ± 256.6 | −780.4 ± 261.3 | −787.0 ± 261.1 | −784.4 ± 260.5 |
| 8 week | −651.2 ± 265.5 | −653.6 ± 258.9 | −671.2 ± 264.6 | −679.0 ± 267.6 | −677.8 ± 268.2 |

| TAC Week | 90 keV | 100 keV | 110 keV | 120 keV | 130 keV | 140 keV |
| --- | --- | --- | --- | --- | --- | --- |
| 0 week | −774.3 ± 248.0 | −773.8 ± 248.2 | −771.8 ± 248.0 | −770.8 ± 248.1 | −769.6 ± 248.2 | −769.0 ± 248.6 |
| 5 week | −782.7 ± 261.4 | −781.4 ± 262.4 | −780.5 ± 263.1 | −779.8 ± 263.7 | −779.3 ± 264.1 | −778.9 ± 264.4 |
| 8 week | −681.0 ± 268.5 | −677.9 ± 269.6 | −675.6 ± 270.2 | −673.7 ± 271.7 | −672.5 ± 271.4 | −669.6 ± 271.6 |

Analysis

All statistical analysis was performed with STATA v12.0 (College Station, Tex.). Multivariate analysis of variance (MANOVA) was performed to test whether the mean CT attenuation values were significantly different between concentration groups (phantom) or disease severity groups (length of TAC exposure, animal). Multivariate regression analysis was performed using animal data to examine the associations of multi-energy CT attenuation values with hypertrophy measured by heart weight to tibia length ratio, and collagen content measured by CVF.

Linear discriminant analysis (LDA) ([16]) is a statistical tool that can be used for classification of collagen content. The distances between multi-dimensional data points (multi-energy attenuation values in this implementation) are calculated. Sets of points that fall close together in the multi-dimensional space might share a particular identifying characteristic and are classified as clusters. LDA was performed using the post-processed mean attenuation values. Data were separated using one energy (70 keV) vs. all eleven energies (40-140 keV) as grouping variables, described as single vs. multi-energy analysis, respectively. Single energy reconstructions were generated at 70 keV to most closely resemble 120 kVp single-energy acquisitions ([17]). Three- and eight-class LDA was performed as follows. For three-class LDA, phantoms were grouped into low (0-7%), moderate (10-20%) and significant (30-62%) collagen concentration categories ([12]). Eight-class LDA was performed by setting each collagen concentration as a separate group. Single and multi-energy three-class LDA was performed with murine heart data grouped according to length of TAC exposure (0, 5, or 8 weeks). Prospective LDA returned a predicted grouping based on CT characteristics for each phantom and animal sample. Correct and incorrect classification rates were calculated as a proportion of total samples.

Results

Phantom Experiments

The MANOVA result indicated a significant difference in mean CT attenuation between collagen concentration groups ($p=0.0039$). The LDA approach described to classify phantoms into one of 3 classes of collagen content (low, moderate, or severe) yielded a correct classification rate of 70% using single energy image analysis; this increased to 80.0% with multi-energy analysis. While 8-class LDA decreased the overall correct classification rate of single-energy analysis to 37.5%, it improved multi-energy analysis accuracy to 92.5%.

Animal Experiments

Figure 4B:
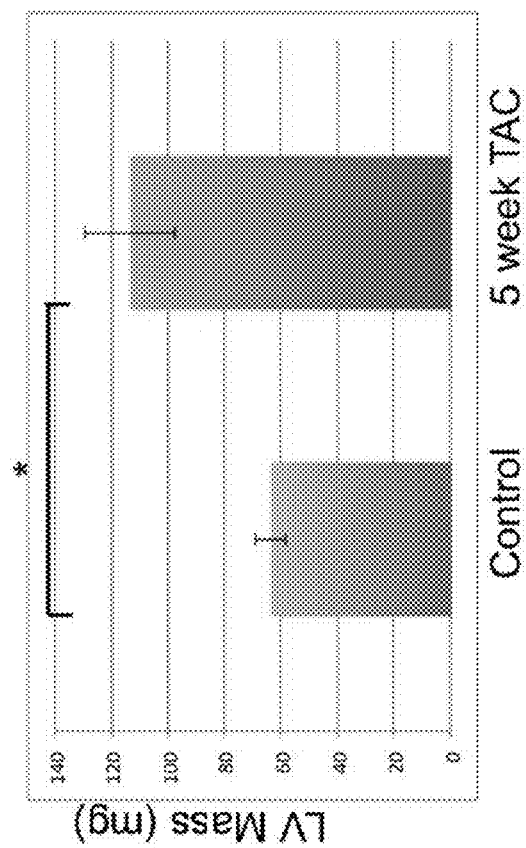
FIGS. 4A, 4B, 4C, and 4D show results of TAC procedures with respect to the example implementations of the present disclosure described for "Example 2". Post-TAC animals demonstrate an exposure dependent increase in heart weight to tibia length ratio (FIG. 4A), LV mass (FIG. 4B), and collagen content (FIG. 4C and FIG. 4D). Asterisks (*) in FIGS. 4A, 4B, and 4D indicate a statistically significant difference ($p<0.05$).
Figure 4A:
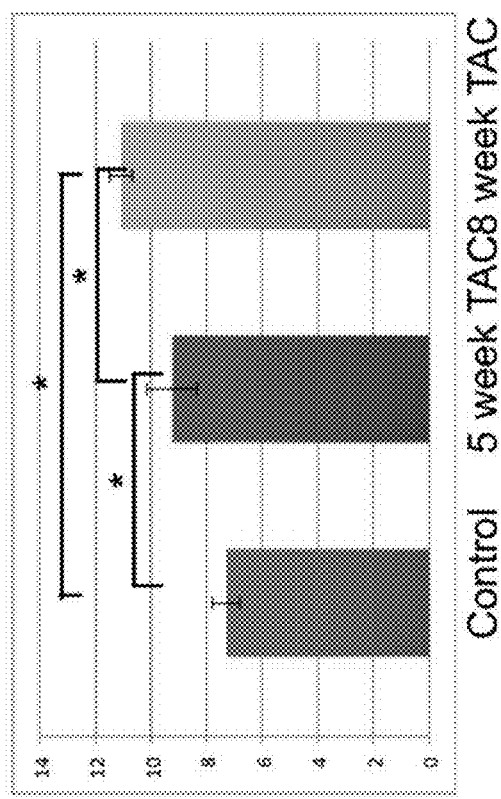
Figure 4C:
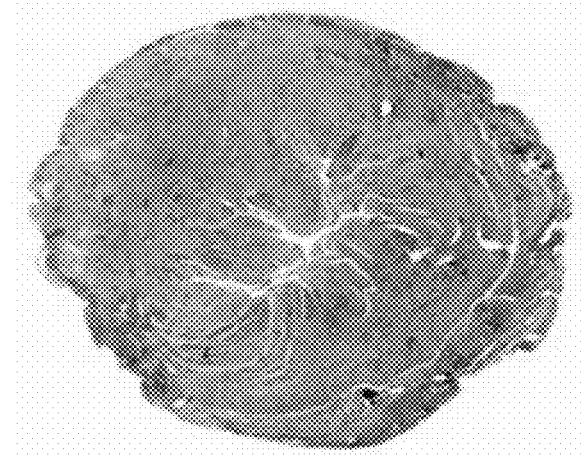
Figure 4C:
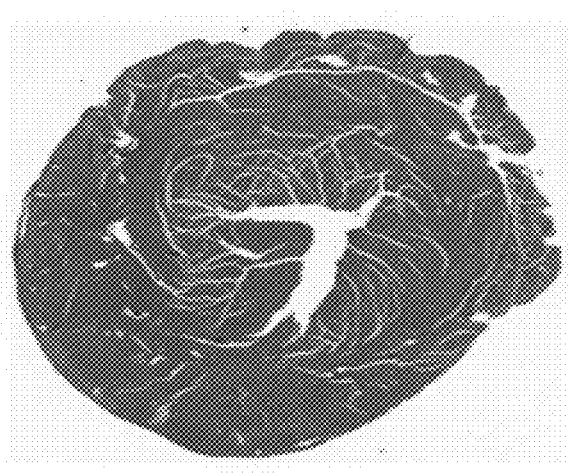
Figure 4C:
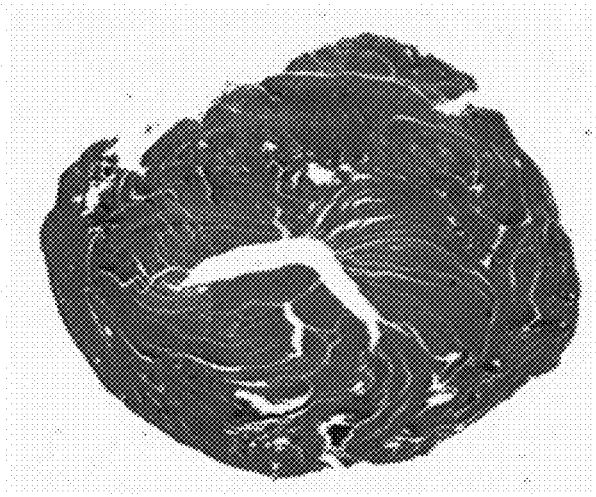
Figure 4D:
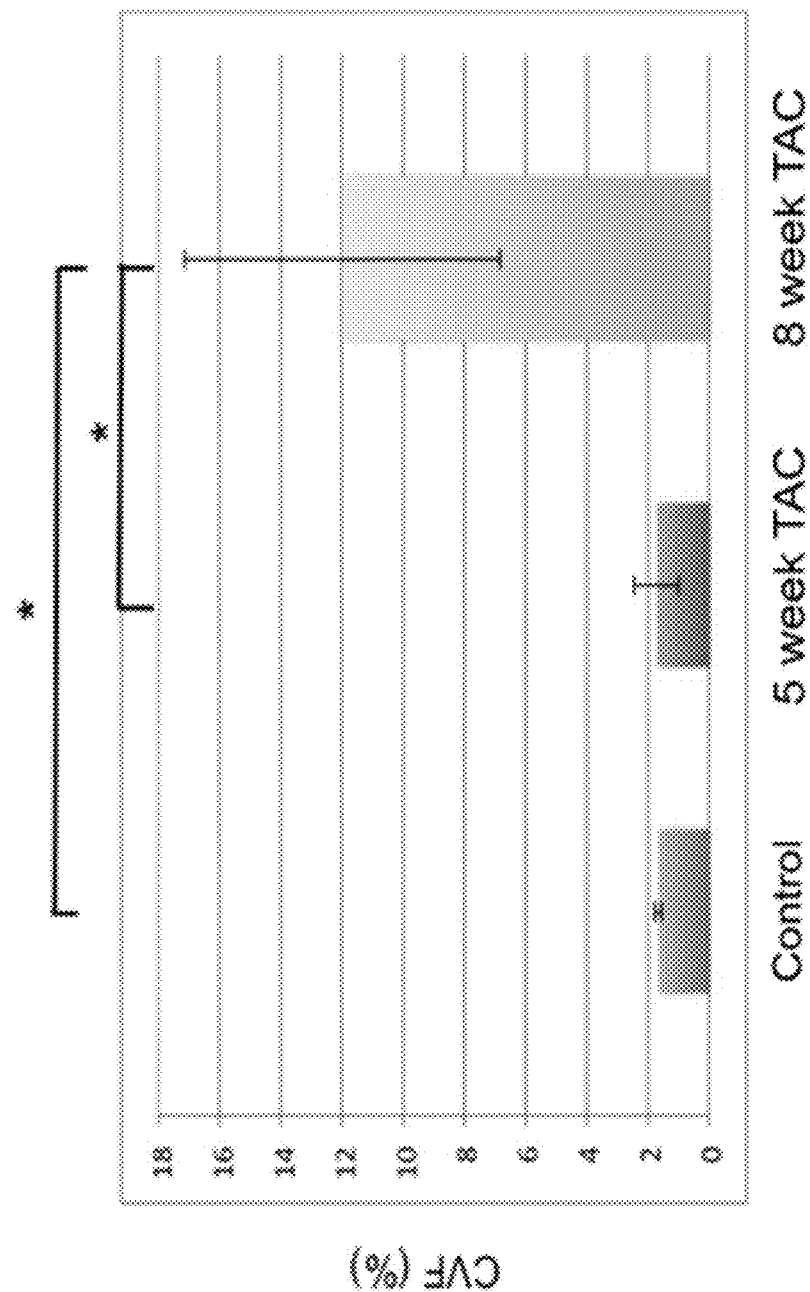
Figure 5:
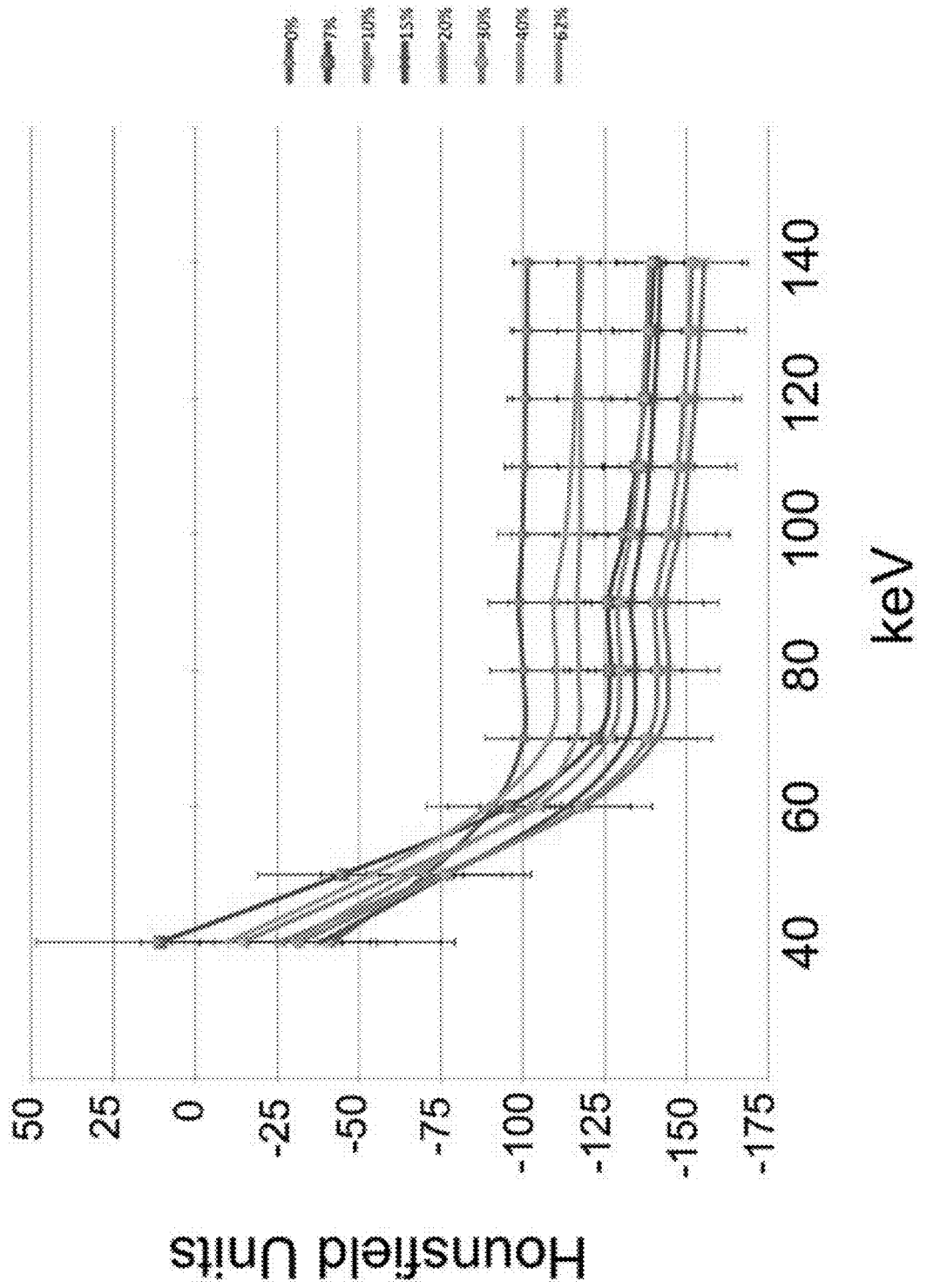
FIG. 5 shows a mean attenuation-energy curve for the phantom experiments with respect to the example implementations of the present disclosure described for "Example 2". Note the overlap of error bars representing standard deviation, across collagen concentration groups when using single energy information alone.
Figure 6:
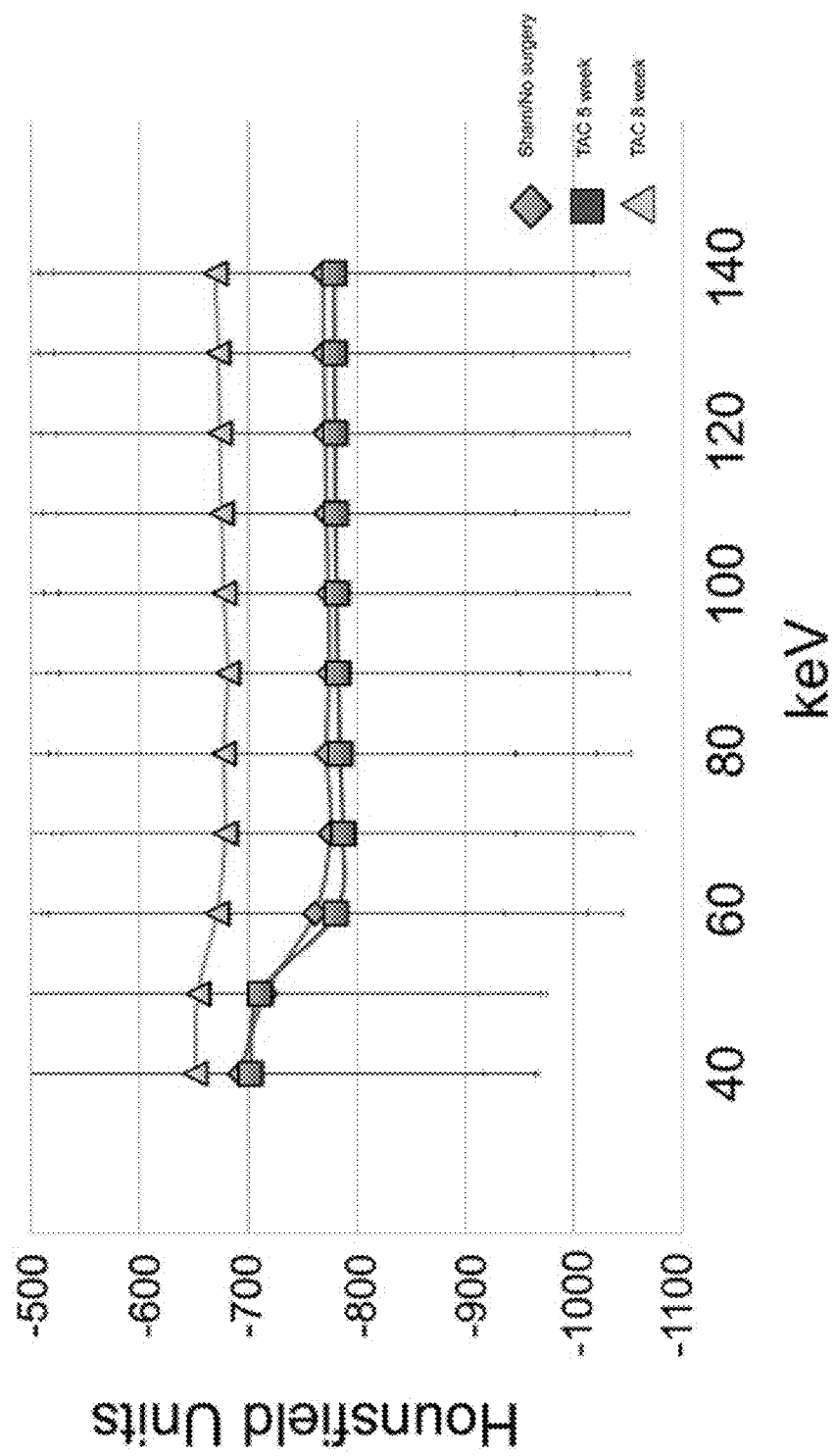
FIG. 6 shows mean attenuation-energy curves for the ex vivo animal experiments with respect to the example implementations of the present disclosure described for "Example 2". Note the large overlap of error bars across the three groups when using single energy information alone.

Echocardiography confirmed progressive cardiac dysfunction with TAC, and LV mass also increased (FIGS. 4A, 4B). Increased CVF by histology confirmed the development of myocardial fibrosis following TAC (see FIGS. 4C and 4D). FIG. 4C particularly shows histology section images illustrating development of myocardial fibrosis (from left to right). The left image corresponds to no or little fibrosis (e.g., "Control" indicated in FIGS. 4A, 4B, and 4D), the center image corresponds to mild or moderate fibrosis (e.g., "5 week TAC" in FIGS. 4A, 4B, and 4D), and the right image corresponds to severe fibrosis (e.g., "8 week TAC" in FIGS. 4A, 4B, and 4D). The MANOVA result indicated that there was no significant difference in mean single energy CT attenuation between animal disease severity groups ($p=0.5454$). However, multivariate regression demonstrated a significant association between 11-energy CT attenuation and collagen value fraction ($R^2=0.9961$, overall F-test $p=0.0025$). The association between multi-energy CT attenuation and hypertrophy was not significant ($R^2=0.7466$, overall F-test $p=0.66$), supporting that the attenuation data reflect tissue characteristics rather than morphology. Multi-energy three-class LDA demonstrated a correct classification rate of 93.3%. Three-class LDA of single energy image data did not perform as well, with a correct classification rate of 33.3%.

Discussion

This Example 2 describes an example implementation of a novel, noninvasive approach to estimate myocardial fibrosis using non-contrast DECT, in accordance with some embodiments of the present disclosure. Validation of the approach was shown in both a phantom model of variable collagen content and an animal model of graded myocardial fibrosis similar to that seen in patients with diffuse interstitial fibrosis. Comparison of phantom collagen concentration and CT attenuation demonstrated a statistically significant difference between groups. Single energy CT attenuations were not statistically different between animal disease severity groups. However, multi-variate regression analysis in animal data demonstrated a significant association between information compiled across multi-energy CT attenuation data and collagen volume fraction.

In addition, LDA analysis was able to correctly classify fibrosis severity in both the phantom and animal models. The multi-energy technique according to example implementations of Example 2 performed better than single energy image-based classification of myocardial fibrosis severity. Superior results were obtained from animal vs. phantom experiments. This may reflect that the fibrillar network of collagen, characteristic of pathophysiological myocardial fibrosis, is not fully replicated in the phantom. The phantom afforded precise manufacturing of myocardial collagen content across a range comparable to that observed in humans; the animal model afforded afforded a realistic replication of interactions between x-ray photons and collagen to yield CT attenuation comparable to what occurs in vivo in humans. Recent studies investigating the potential of DECT for tissue characterization have proposed that low-energy attenuation measurements afford greater distinction among tissue components, compared to higher-energy attenuation measurements ([18,19]). However, the data presented herein do not show a consistent change in attenuation behavior due to collagen concentration or disease severity at lower vs. higher energy levels. Collagen deposition appears to alter the overall relationship between x-ray photon energy and attenuation, a difference that can be identified by analyzing data in a multi-energy, multi-dimensional space.

Further studies may investigate the specificity of this classifier in rating collagen content compared to other materials that may deposit in diseased myocardium, noting that measurements presented herein for Example 2 fall outside attenuation values for fat. Further studies may also include comparison to contrast-enhanced DECT and MRI-based methods for myocardial fibrosis estimation.

Diffuse myocardial fibrosis contributes to abnormal cardiac mechanics and electrophysiological properties, both incurring risk of adverse events such as heart failure and arrhythmias. The presence of myocardial fibrosis by late gadolinium enhancement (LGE) CMR has proven prognostic value beyond measures of contractility such as ejection fraction ([20]), and T1 mapping may better demonstrate diffuse fibrosis compared to LGE. However, some proportion of patients requiring myocardial tissue characterization have sufficient claustrophobia to preclude entry into even larger bore MR scanners. Further, despite decades of work, MR coronary angiography remains limited compared to computed tomography angiography (CTA) for reliable evaluation of the entire epicardial coronary tree. The inventors have previously shown that coronary artery calcium scores derived from non-contrast DECT are comparable to those obtained with single energy CT, with an estimated radiation exposure within the range used for protocols such as CT perfusion and other advanced cardiac applications. ([17]) Thus, in patients who are referred to rule-out coronary artery disease (CAD) in the setting of new-onset cardiomyopathy or ventricular arrhythmia, the typical non-contrast scan that precedes CTA may be replaced with a non-contrast DECT scan followed by CTA that can offer combined assessment of both epicardial CAD and myocardial fibrosis in a single noninvasive imaging procedure.

CONCLUSION

The specific configurations, choice of materials and the size and shape of various elements can be varied according to particular design specifications or constraints requiring a system or method constructed according to the principles of the present disclosure. Such changes are intended to be embraced within the scope of the present disclosure. The presently disclosed embodiments, therefore, are considered in all respects to be illustrative and not restrictive. The patentable scope of certain embodiments of the present disclosure is indicated by the appended claims, rather than the foregoing description, and all changes that come within the meaning and range of equivalents thereof are intended to be embraced therein.

REFERENCE LIST

[1] Saffitz J E. The pathology of sudden cardiac death in patients with ischemic heart disease—arrhythmology for anatomic pathologists. Cardiovasc Pathol official J Soc Cardiovasc Pathol. 2005; 14:195-203.

[2] Mewton N, Liu C Y, Croisille P, Bluemke D, Lima J A. Assessment of myocardial fibrosis with cardiovascular magnetic resonance. J Am Coll Cardiol. 2011; 57:891-903.

[3] Priori S G, Blomstrom-Lundqvist C, Mazzanti A, et al. 2015 ESC guidelines for the management of patients with ventricular arrhythmias and the prevention of sudden cardiac death. The task force for the management of patients with ventricular arrhythmias and the prevention of sudden cardiac death of the European society of cardiology. G Ital Cardiol. 2016; 17:108-170.

[4] Yi C J, Wu C O, Tee M, et al. The association between cardiovascular risk and cardiovascular magnetic resonance measures of fibrosis: the Multi-Ethnic Study of Atherosclerosis (MESA). J Cardiovasc Magn. Reson official J Soc Cardiovasc Magn. Reson. 2015; 17:15.

[5] Whittaker P, Kloner R A, Boughner D R, Pickering J G. Quantitative assessment of myocardial collagen with picrosirius red staining and circularly polarized light. Basic Res Cardiol. 1994; 89:397-410.

[6] Diao K Y, Yang Z G, Xu H Y, et al. Histologic validation of myocardial fibrosis measured by T1 mapping: a systematic review and meta-analysis. J Cardiovasc Magn. Reason official J Soc Cardiovasc Magn. Reson. 2016; 18:92.

[7] Johnson T R, Krauss B, Sedlmair M, et al. Material differentiation by dual energy CT: initial experience. Eur Radiol. 2007; 17:1510-1517.

[8] Lamb P, Sahani D, Fuentes-Oreego J, Patino M, Ghosh A, Mendonca P. Stratification of patients with liver fibrosis using dual-energy CT. IEEE Trans Med Imaging. 2015; 34(3):807-815.

[9] Bandula S, White S K, Flett A S, et al. Measurement of myocardial extracellular volume fraction by using equilibrium contrast-enhanced CT: validation against histologic findings. Radiology. 2013; 269:396-403.

[10] Nacif M S, Kawel N, Lee J J, et al. Interstitial myocardial fibrosis assessed as extracellular volume fraction with low-radiation-dose cardiac CT. Radiology. 2012; 264:876-883.

[11] Hong Y J, Kim T K, Hong D, et al. Myocardial characterization using dual-energy CT in doxorubicin-induced DCM: comparison with CMR t1-mapping and histology in a rabbit model. JACC Cardiovasc Imaging. 2016; 9:836-845.

[12] Ying X, Lee K, Li N, Corbett D, Mendoza L, Frangogiannis N G. Characterization of the inflammatory and fibrotic response in a mouse model of cardiac pressure overload. Histochem Cell Biol. 2009; 131:471-481.

[13] Stuckey D J, McSweeney S J, Thin M Z, et al. T(1) mapping detects pharmacological retardation of diffuse cardiac fibrosis in mouse pressure-overload hypertrophy. Circ Cardiovasc Imaging. 2014; 7:240-249.

[14] deAlmeida A C, van Oort R J, Wehrens X H T. Transverse aortic constriction in mice. J Vis Exp JoVE. 2010.

[15] Zhang D, Li X, Liu B. Objective characterization of GE discovery CT750 HD scanner: gemstone spectral imaging mode. Med Phys. 2011; 38:1178-1188.

[16] Fukunaga K. Introduction to Statistical Pattern Recognition. second ed. Boston: Academic Press; 1990:124-181.

[17] Kumar V, Min J K, He X, Raman S V. Computation of calcium score with dual-energy computed tomography: a phantom study. J Comput Assisted Tomogr. 2017; 41:156-158.

[18] Rodriguez-Granillo G A, Campisi R, Deviggiano A, et al. Detection of myocardial infarction using delayed enhancement dual-energy CT in stable patients. AJR Am J Roentgenol. 2017:1-10.

[19] Reynoso E, Rodriguez-Granillo G A, Capunay C, Deviggiano A, Meli F, Carrascosa P. Spectral signal density of carotid plaque using dual-energy computed tomography. J Neuroimaging Official J Am Soc Neuroimaging. 2017; 27:511-516.

[20] Gulati A, Jabbour A, Ismail T F, et al. Association of fibrosis with mortality and sudden cardiac death in patients with nonischemic dilated cardiomyopathy. J Am Med Assoc. 2013; 309:896-908.

[21] Kumar V, McElhanon K E, Min J K, et al. Non-contrast estimation of diffuse myocardial fibrosis with dual energy CT: A phantom study. J Cardiovasc Comput Tomogr. 2018; 12:74-80.

[22] Kramer C M, Barkhausen J, Flamm S D, Kim R J, Nagel E. Standardized cardiovascular magnetic resonance (CMR) protocols 2013 update. Journal of Cardiovascular Magnetic Resonance. 2013; 15:91.

[23] Xue H, Shah S, Greiser A, et al. Motion correction for myocardial T1 mapping using image registration with synthetic image estimation. Magn Reson Med. 2012; 67:1644-1655.

[24] Puntmann V O, Peker E, Chandrashekhar Y, Nagel E. T1 mapping in characterizing myocardial disease: a comprehensive review. Circ Res. 2016; 119:277-299.

[25] Wong T C, Piehler K, Meier C G, et al. Association between extracellular matrix expansion quantified by cardiovascular magnetic resonance and short-term mortality. Circulation. 2012; 126:1206-1216.

[26] Schulz-Menger J, Bluemke D A, Bremerich J, et al. Standardized image interpretation and post processing in cardiovascular magnetic resonance: Society for Cardiovascular Magnetic Resonance (SCMR) board of trustees task force on standardized post processing. J Cardiovasc Magn Reson. 2013; 15:35.

[27] Haaf P, Garg P, Messroghli D R, Broadbent D A, Greenwood J P, Plein S. Cardiac T1 mapping and extracellular volume (ECV) in clinical practice: a comprehensive review. J Cardiovasc Magn Reson. 2016; 18:89.

[28] J. H. Hubbell and S. M. Seltzer. Tables of X-Ray Mass Attenuation Coefficients and Mass Energy-Absorption Coefficients from 1 keV to 20 MeV for Elements Z=1 to 92 and 48 Additional Substances of Dosimetric Interest. NIST Standard Reference Database 126. Last updated July 2004. Available online, internet: https://www.nist.gov/pml/x-ray-mass-attenuation-coefficients (last accessed Dec. 5, 2018).

What is claimed is:

1. A method for non-invasively assessing a myocardial region of a subject by computed tomography (CT), the method comprising:
    acquiring non-contrast imaging data for a myocardial region of a subject using dual energy computed tomography (DECT) scanning;
    reconstructing, from the acquired non-contrast imaging data, monochromatic images for a plurality of energy levels in a range of energy levels;
    determining, based at least in part on the image reconstruction, attenuation values for each respective energy level of the plurality of energy levels;
    performing at least one of detection and quantification of myocardial fibrosis based at least in part on differences in the attenuation values across the plurality of energy levels; and
    performing a linear discriminant analysis on the attenuation values to classify the myocardial fibrosis, wherein the linear discriminant analysis comprises:
        calculating distances between multi-energy attenuation values in multi-dimensional space; and
        based on the calculated distances, clustering attenuation values that fall close together in the multi-dimensional space, wherein each cluster shares at least one particular identifying characteristic of an associated material.

2. The method of claim 1, wherein classifying the myocardial fibrosis comprises determining a classification of the severity of the myocardial fibrosis.

3. The method of claim 1, wherein determining the attenuation values for the plurality of energy levels comprises performing a material decomposition technique.

4. The method of claim 1, wherein the detection and/or quantification of the myocardial fibrosis comprises differentiating collagen from other materials in the myocardial region of the subject.

5. The method of claim 1, wherein the range of energy levels is from about 40 keV to about 140 keV.

6. The method of claim 1, wherein the dual energies for the CT scanning correspond to x-ray tube voltages of about 80 kVp and about 140 kVp.

7. The method of claim 1, wherein the subject is a human.

8. A method for non-invasively assessing a region of interest of a subject by computed tomography (CT), the method comprising:
    acquiring non-contrast imaging data corresponding to the region of interest of the subject using dual energy computed tomography (DECT) scanning;
    reconstructing, from the acquired non-contrast imaging data, monochromatic images for a plurality of energy levels in a range of energy levels;
    determining, based at least in part on the image reconstruction, attenuation values for each respective energy level of the plurality of energy levels;
    performing at least one of detection and quantification of a material of interest in tissue of the subject in the region of interest, based at least in part on differences in the attenuation values across the plurality of energy levels; and
    performing a linear discriminant analysis on the attenuation values to perform the detection and/or quantification of the material of interest, wherein the linear discriminant analysis comprises:
        calculating distances between multi-energy attenuation values in multi-dimensional space; and
        based on the calculated distances, clustering attenuation values that fall close together in multi-dimensional space, wherein each cluster shares at least one particular identifying characteristic of an associated material.

9. The method of claim 8, wherein the material of interest in the tissue comprises at least one of iron, fat, inflammatory cells, and amyloid protein.

10. The method of claim 8, further comprising identifying and/or classifying a condition of the subject based on the detection and/or quantification of the material of interest.

11. The method of claim 10, wherein the condition of the subject comprises at least one of: myocardial fibrosis; cirrhosis in the liver; fibrosis in the kidney; iron overload in the heart, skeletal muscle, liver, pancreas, or pituitary gland; amyloidosis in the heart, skin, kidney, brain, or liver.

12. The method of claim 8, wherein the region of interest comprises at least part of the heart, pancreas, liver, spleen, kidney, brain, lungs, skin, and/or skeletal muscle of the subject.

13. The method of claim 12, wherein the detecting and/or quantifying of the material of interest in the tissue comprises detecting the associated material from a respective at least one shared, particular identifying characteristic.

14. The method of claim 8, wherein determining the attenuation values for the plurality of energy levels comprises performing a material decomposition technique.

15. The method of claim 8, wherein performing the detection and/or quantification of the material of interest in the tissue of the subject comprises differentiating a particular material from other materials in the region of interest of the subject.

16. The method of claim 8, wherein the range of energy levels is from about 40 keV to about 140 keV.

17. The method of claim 8, wherein the dual energies for the DECT scanning correspond to x-ray tube voltages of about 80 kVp and about 140 kVp.

18. The method of claim 8, wherein the subject is a human.

* * * * *